US006632437B1

United States Patent
Schneerson et al.

(12)

(10) Patent No.: US 6,632,437 B1
(45) Date of Patent: Oct. 14, 2003

(54) IMMUNOGENIC POLYSACCHARIDE-PROTEIN CONJUGATES CONTAINING POLY α(2→8), α(2→9) NEUNAC CAPSULAR POLYSACCHARIDES

(75) Inventors: Rachel Schneerson, Bethesda, MD (US); John B. Robbins, Chevy Chase, MD (US); J. N. Sarvamangala Devi, Columbia, MD (US)

(73) Assignee: The United States of America as represented by the Department of Health and Human Services, DC (US)

( * ) Notice: Subject to any disclaimer, the term of this patent is extended or adjusted under 35 U.S.C. 154(b) by 0 days.

(21) Appl. No.: 08/153,263

(22) Filed: Nov. 15, 1993

Related U.S. Application Data (63) Continuation of application No. 07/667,170, filed on Mar. 12, 1991, now abandoned.

(51) Int. Cl.$^7$ ............................ A61K 39/385; A61K 39/395; A61K 39/108; C08H 1/00
(52) U.S. Cl. ............................... 424/193.1; 424/137.1; 424/194.1; 424/197.11; 424/241.1; 530/403; 530/404; 530/405; 530/406
(58) Field of Search .......................... 424/193.1, 194.1, 424/197.11, 241.1, 137.1; 530/403–406

(56) References Cited

U.S. PATENT DOCUMENTS

| | | | | |
|---|---|---|---|---|
| 4,356,170 A | * | 10/1982 | Jennings et al. | 424/92 |
| 4,619,828 A | * | 10/1986 | Gordon | 424/92 |
| 4,695,624 A | * | 9/1987 | Marburg et al. | 530/395 |
| 4,711,779 A | * | 12/1987 | Porro et al. | 424/92 |
| 5,034,516 A | * | 7/1991 | Roy et al. | 536/4.1 |

OTHER PUBLICATIONS

Osband et al (1990) Immunology Today 11(6):193–5.*
Gould et al (1989) J. Natl Cancer Inst. 81(10) 775–81.*
Dictionary of Immunology, 3rd ed, ed by WJ Herbert et al Blackwell Scientific Publications, Oxford 1985 pp. 65–66
Aldrich Catalog 1992–1993 p. 33 product No. 21782–4 Adipic dihydrafide.*
Häyrinen et al (1989) Molecular Immunology 26(6): 523–529.*
Chu et al (1983) Infection and Immunity 40(1):245–256.*
Bitter–Suermann et al (1987) Immunol. Res. 6:225–237.*
"Availability of Meningococcal Vaccine in Single–Dose Vitals for Travelers and High–Risk Persons", Morbidity and Mortality Weekly Report, Mass. Medical Society, vol. 39, No. 2, Oct. 26, 1990 p. ?.
Schlech, et al. "Bacterial Meningitis and Meningococcemia—United States, 1978", Morbidity and Mortality Weekly Report, Jun. 22, 1979, vol. 28, No. 24 pp 277–279.
Poolman et al., "Meningococcal Serotypes and Serogroup B Disease in North–West Europe", The Lancet, Sep. 6, 1986 pp. 555–557.

Brandtzaeg et al., "Plasma Endotoxin as a Predictor of Multiple Organ Failure and Death in Systemic Meningococcal Disease", The Journal of Infectious Diseases, vol. 159, No. 2, Feb. 1989, pp. 195–204.
Mendelman et al., "Genetic Diversity of Penicillin G–Resistant Neisseria Meningitidis from Spain", Infection and Immunity, vol. 57, No. 4, Apr. 1989, pp. 1025–1029.
Jennings et al., "Immunochemistry of Groups A, B, and C Meningococcal Polysaccaride–Tetanus Toxoid Conjugates", The Journal of Immunology, vol. 127, No. 3, Sep. 1981 pp 1011–1018.
Jennings et al., "N–Propionylated Group B Meningococcal Polysaccharide Mimics a Unique Epitope on Group B Neisseria Meningitidis", J. Exp. Med. vol. 165, Apr. 1987, pp. 1207–1211.
Frasch et al., "Antibody Response of Adults to an Aluminum Hydroxide–Adsorbed Neisseria Meningtidis Serotype 2b Protein–Group B Polysaccharide Vaccine", Journal of Infectious Diseases, vol. 158, No. 4, Oct. 1988 pp. 710–718.
Lifely, et al., "Immunogenicity in Adult Males of a Neisseria Meningitidis Group B Vaccine Composed of Poly–Saccharide Complexed with Outer Membrane Proteins", 60 Vaccine, vol. 9, Jan. 1991 pp. 60–66.
Zollinger et al., "Safety and Immunogenicity of a Neisseria Meningitidis Type 2 Protein Vaccine in Animals and Humans", The Journal of Infectious Diseases, vol. 137, No. 6, Jun. 1978 pp. 728–739.
Jennings, et al., "Conjugation of Meningococcal Lipopolysaccharide R–Type Oligosaccharides to Tetanus Toxoid as Route to a Potential Vaccine Against Group B Neisseria Meningitidis", Infection and Immunity, Jan. 1984, vol. 43, No. 1, pp. 407–412.
Verheul et al., "Preparation, Characterization and Immunogenicity of Meningococcal Immunotype L2 and L3,7,9, Phosphoethanolamine Group–Containing Oligosaccharide–Protein Conjugates", Infection and Immunity, vol. 59, No. 3, Mar. 1991, pp. 843–851.
Adlam et al., "Production of Colominic Acid by Pasteurella Haemolytica Serotype A2 Organisms", FEMS Microbiology Letters 42 (1987), pp. 23–25.
Frank, "The Role of Pasteurella Haemolytica in the Bovine Respiratory Disease Complex", Veterinary Medicine, Sep. 1986, pp. 838–846.
Frank, "Serotypes of Pasteurella Haemolytica in Sheep in the Midwestern United States", Amer. Journal of Veterinary Res., vol. 43, No. 11, pp. 2035–2037 1982.

(List continued on next page.)

*Primary Examiner*—Ponnathapu Achutamurthy
(74) *Attorney, Agent, or Firm*—Birch, Stewart, Kolasch & Birch, LLP (57) ABSTRACT

The present invention relates to a polysaccharide-protein conjugate. The invention also relates to a method of using the conjugate to prevent systemic infections. The invention further relates to a pharmaceutical composition. The invention also relates to a method of producing a polysaccharide-protein conjugate.

38 Claims, 3 Drawing Sheets

OTHER PUBLICATIONS

Fraser et al., "Prevalence of Pasteurella Haemolytica Serotypes Isolated from Ovine Pasteurellosis in Britain", Veterinary Record, (1982), 110: 560–561.

Gilmour et al., "The Development of Vaccines Against Pneumonic Pasteurellosis in Sheep", The Veterinary Record, Jan. 6, 1979, p. 15.

Thompson et al., "Serotypes of Pasteurella Haemolytica in Ovine Pasteurellosis", Research in Veterinary Science 1977, 22, pp. 130–131.

Jennings et al., "Induction of Meningococcal Group B Polysaccharide–Specific IgG Antibodies in Mice by Using an N–Propionylated B Polysaccharide–Tetanus Toxoid Conjugate Vaccine", Journal of Immunology, vol. 137, Sep. 1, 1986, pp. 1708–1713.

Moreno et al., "Immunity and Projection of Mice Against Neisseria Meningitidis Group B by Vaccination, Using Polysaccharide Complexed with Outer Membrane Proteins: A Comparision with Purified B Polysaccharide", Infection and Immunity, vol. 47, No. 2, Feb. 1985, pp. 527–533.

* cited by examiner

IMMUNOGENIC POLYSACCHARIDE-PROTEIN CONJUGATES CONTAINING POLY α(2→8), α(2→9) NEUNAC CAPSULAR POLYSACCHARIDES

This is a continuation of co-pending application Ser. No. 07/667,170, filed on Mar. 12, 1991, abandoned.

BACKGROUND OF THE INVENTION

1. Field of the Invention

The present invention relates, in general, to polysaccharide-protein conjugates and vaccines. In particular the present invention relates to polysaccharide-protein conjugates that elicit serum IgG and IgM antibodies to poly α(2→8) NeuNAc, or to both poly α(2→8) NeuNAc and poly α(2→9) NeuNAc, or to poly α(2→8),α(2→9) NeuNAc.

2. Background Information

*Neisseriae meningitidis* are a major cause of systemic infections, especially meningitis, in humans. Capsular polysaccharide (CP) vaccines are licensed for meningococcal groups A,C,Y and W135. Diseases caused by group B meningococci continue to occur in endemic and epidemic forms and remain an important health problem (Gotschlich, E. C. (1984) in Bacterial Vaccines. Ed. Germanier (Academic Press, NY) pp. 237–255; Peltola, H. (1983) Rev. Infect. Dis. 5, 71–91; Poolman, J. T. et al. (1986) Lancet, ii,555–557). *Escherichia coli* (*E. coli*) K1 is a major cause of neonatal meningitis, upper urinary tract infections and systemic infections in hospitalized patients and in domesticated and laboratory animals (Robbins, J. B. et al. (1974) N. Eng. J. Med. 290, 1216–1220; Kaijser, B. et al. (1977) Lancet i, 663–664; Cross, A. S. et al. (1984) J. Infect. Dis. 149, 184–193; Ørskov, I., & Ørskov, F. (1985) J. Hyg. Camb. 95, 551–575). Despite antibiotic treatment and supportive care, meningitis caused by these two pathogens continues to exert a high morbidity, including permanent CNS injury, and mortality (Peltola, H. (1983) Rev. Infect. Dis. 5, 71–91; Schneerson, R. (1988) in Understanding Mental Retardation. ed. Kavanagh, J. F. (Paul Brookes Publishing Co. Baltimore), pp. 237–249; Brandtzaeg, P. et al. (1989) J. Infect. Dis. 159, 195–204; McCracken, G. H., Jr. et al. (1974) Lancet, ii, 246–250).

The CP of Group B meningococci and of *E. coli* K1 are identical (poly α(2→8) NeuNAc) and serve as essential virulence factors and protective antigens for both pathogens (Grados, O., & Ewing, W. H. (1970) J. Infect. Dis. 122, 100–103; Kasper, D. L. et al. (1973) J. Immunol. 110, 262–268; Bhattacharjee, A. K. et al. (1975) J. Biol. Chem. 250, 1926–1932; Robbins, J. B. et al. (1974) N. Eng. J. Med. 290, 1216–1220). Poly α(2→8) NeuNAc is also a surface antigen of *Moraxella nonliquefaciens* and *Pasteurella haemolytica,* serotype A-2 (Bøvre, K. et al. (1983) NIHP Annals. 6, 65–73; Devi, S. J. N. et al. (1991) Infect. Immun. 59, 732–736; Adlam, C. et al. (1987) FEMS Microbiol. Lett. 42, 23–25). The latter is the major cause of outbreaks of pasteurellosis in young lambs which suggests that poly α(2→8) NeuNAc may serve as a virulence factor for yet another bacterial species.

Attempts to induce protective immunity to group B meningococci and *E. coli* K1 have been thwarted because poly α(2→8) NeuNAc, alone or complexed to outer membrane proteins, induced low and transient levels of IgM antibodies (Kasper, D. L. et al. (1973) J. Immunol. 110, 262–268; Wyle, F. A. et al. (1972) J. Infect. Dis. 126, 514–522; Zollinger, W. D. et al. (1979) J. Clin. Invest. 63, 836–842; Moreno, C. et al. (1985) Infect. Immun. 47, 527–533; Frasch, C. E. et al. (1988) J. Infect. Dis. 158, 710–718; Lifely, M. R. et al. (1991) Vaccine 9, 60–66). Covalent attachment of periodate-treated (Jennings, H. & Lugowski, C. (1981) J. Immunol. 127, 1011–1018) or acid-hydrolyzed poly α(2→8) NeuNAc (Porro, M. et al. (1983) Med. Trop. 43, 129–132) to a protein also failed to elicit antibodies to this antigen. Further, this CP has been considered as a "self antigen", because α(2→8) NeuNAc is found as monomers or dimers on glycoproteins and gangliosides in adults and up to ≈11 residues in fetal tissues including N-CAMs (Finne, J. et al. (1983) Lancet, ii, 355–357; Finne, J. et al. (1987) J. Immunol. 138, 4402–4407; Soderstrom, T. et al. (1984) N. Eng. J. Med. 310, 726–727). Accordingly, investigators have studied other components, such as LPS, outer membrane proteins and iron-binding proteins, or chemically modified poly α(2→8) NeuNAc, as potential vaccines (Zollinger, W. D. et al. (1979) J. Clin. Invest. 63, 836–842; Moreno, C. et al. (1985) Infect. Immun. 47, 527–533; Frasch, C. E. et al. (1988) J. Infect. Dis. 158, 710–718; Jennings, H. J. et al. (1984) Infect. Immun. 43, 407–412; Jennings, H. J. et al. (1986) J. Immunol. 137, 1708–1713; Frasch, C. E. (1989) Clin. Microbiol. Rev. 2(Suppl), S134-S138).

Most newborns and adults have bactericidal antibodies to the three major serogroups (A,B,C) of meningococci (Goldschneider, I. et al. (1969) J. Exp. Med. 129, 1307–1326); most of the bactericidal activity, including of group B meningococci, was removed by adsorption with the homologous CP (Frasch, C. E. et al. (1988) J. Infect. Dis. 158, 710–718; Brandt, B. L. et al. (1972) J. Immunol. 108, 913–920; Kasper, D. L. et al. (1973) J. Infect. Dis. 127, 378–387; Skevakis, L. et al. (1984) J. Infect. Dis. 149, 387–396). The peak incidence of disease caused by meningococci, including group B, is when the maternally-derived antibodies have waned and the adult levels have not yet developed (Gotschlich, E. C. (1984) in Bacterial Vaccines. Ed. Germanier (Academic Press, NY) pp. 237–255; Goldschneider, I. et al. (1969) J. Exp. Med. 129, 1307–1326). Rises in poly αa(2→8) NeuNAc antibodies, including those of the IgG isotype, are detectable in patients convalescent from group B meningococcal meningitis (Wyle, F. A. et al. (1972) J. Infect. Dis. 126, 514–522; Zollinger, W. D. et al. (1979) J. Clin. Invest. 63, 836–842; Frasch, C. E. et al. (1988) J. Infect. Dis. 158, 710–718; Skevakis, L. et al. (1984) J. Infect. Dis. 149, 387–396; Craven, D. E. et al. (1982) Infect. Immun. 37, 132–137; Mandrell, R. E. & Zollinger, W. D. (1982) J. Immunol. 129, 2172–2178; Leinonen, M. & Frasch, C. E. (1982) Infect. Immun. 38, 1203–1207). Polyclonal and monoclonal (mAb) poly α(2→8) NeuNAc antibodies were raised in animals by multiple intravenous injections of bacteria (Robbins, J. B. et al. (1974) N. Eng. J. Med. 290, 1216–1220; Moreno, C. et al. (1985) Infect. Immun. 47, 527–533; Mandrell, R. E. & Zollinger, W. D. (1982) J. Immunol. 129, 2172–2178; Allen, P. Z. et al. (1982) J. Clin. Microbiol. 15, 324–329; Craven, D. E. et al. (1979) J. Clin. Microbiol. 10, 302–307; Frosch, M. et al. (1985) Proc. Natl. Acad. Sci. (USA) 82, 1194–1198). Monoclonal antibodies to this antigen were identified in a healthy 81 year old male and from hybridoma cultures (Kabat, E. A. et al. (1986) J. Exp. Med. 164, 642–654; Kabat, E. A. et al. (1988) J. Exp. Med. 168, 699–711; Raff, H. V. et al. (1988) J. Infect. Dis. 157, 118–126). These antibodies exert biologic activities which have been correlated with protective immunity; 1) complement-dependent bacteriolysis on Group B meningococci (Gotschlich, E. C. (1984) in Bacterial Vaccines. Ed. Germanier (Academic Press, NY) pp. 237–255;

Goldschneider, I. et al. (1969) J. Exp. Med. 129, 1307–1326); 2) protection against lethal infection of rodents by *E. coli* K1 (Robbins, J. B. et al. (1974) N. Eng. J. Med. 290, 1216–1220; Glode, M. P. et al. (1977) Infect. Immun. 16, 75–80; Kim, K. S. et al. (1985) Infect. Immun. 50, 734–737).

Figure 1:
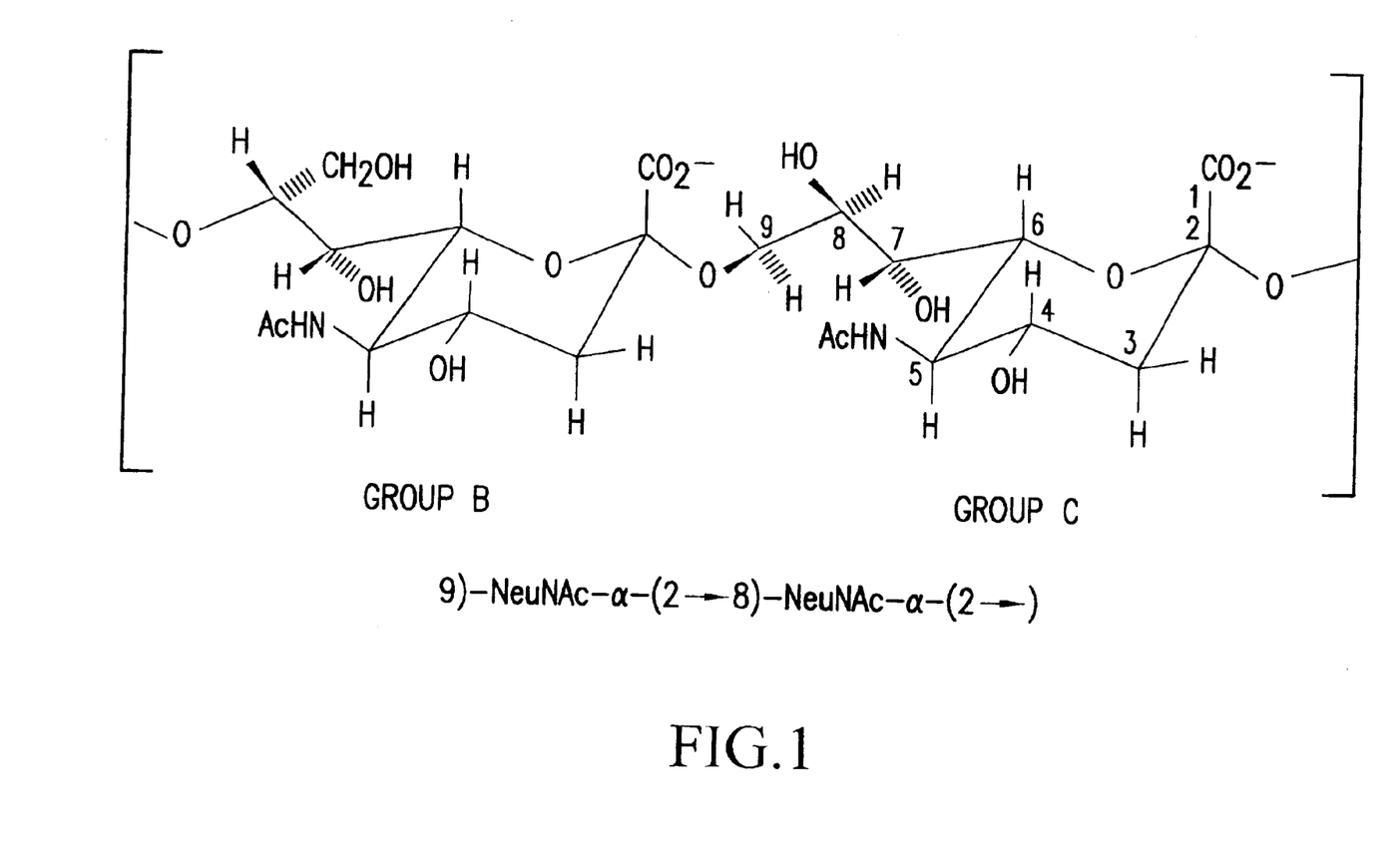
FIG. 1. Structure of the *Escherichia coli* K92 capsular polysaccharide: a disaccharide repeat unit of alternating poly α(2→8),α(2→9) NeuNAc (Egan, W., et al. (1977) Biochem. (USA) 13, 3687–3692). The structure of this polysaccharide can be written as 9)-NeuNac-α-(2→8)-NeuNac-α-(2α).

There are two other bacterial NeuNAc polymers: 1) group C *N. meningitidis* CP composed of poly α(2→9) NeuNAc; most strains are variably O-acetylated at C7 or C8 (Bhattacharjee, A. K. et al. (1975) J. Biol. Chem. 250, 1926–1932). Although differing from poly α(2→8) NeuNAc only by linkage, poly α(2→9) NeuNAc is immunogenic and is a licensed vaccine against group C meningococci (World Health Organization Expert Committee on Biological Standardization. (1977) Technical Report Series, 610. WHO, Geneva, Switzerland); 2) *E. coli* K92 CP (FIG. 1) with the disaccharide repeat unit of alternating α(2→8),α(2→9) NeuNAc (The structure of this polysaccharide can be written as 9)-NeuNAc-α-(2→8)-NeuNAc-α-(2→.) (Robbins, J. B. et al. (1972) Infect. Immun. 6, 651–656; Glode, M. P. et al. (1977) J. Infect. Dis. 135, 94–102; Egan, W. et al. (1977) Biochem. (USA) 16, 3687–3692; Glode, M. P. et al. (1979) J. Infect. Dis. 139, 52–59). Both group B and group C meningococcal antisera precipitate with *E. coli* K92 CP (Glode, M. P. et al. (1977) J. Infect. Dis. 135, 94–102; Egan, W. et al. (1977) Biochem. (USA) 16, 3687–3692; Glode, M. P. et al. (1979) J. Infect. Dis. 139, 52–59). Multiple i.v. injections of killed *E. coli* K92 bacteria induced precipitating antibodies to poly α(2→9) NeuNAc and to poly α(2→8),α(2→9) NeuNAc but not to poly α(2→8) NeuNAc (Glode, M. P. et al. (1977) J. Infect. Dis. 135, 94–102). Injection of *E. coli* K92 CP induced poly α(2→9) NeuNAc antibodies in adult volunteers; antibodies to poly α(2→8) NeuNAc were not measured (Glode, M. P. et al. (1979) J. Infect. Dis. 139, 52–59).

SUMMARY OF THE INVENTION

It is a general object of this invention to provide a polysaccharide-protein conjugate and a vaccine.

It is a specific object of this invention to provide a polysaccharide-protein conjugate capable of eliciting serum IgG and IgM antibodies to poly α(2→8) NeuNAc, or to both poly α(2→8) NeuNAc and poly α(2→9) NeuNAc, or to poly α(2→8),α(2→9) NeuNAc.

It is a further object of this invention to provide a pharmaceutical composition suitable for use in preventing systemic infections.

It is another object of this invention to provide a method of preventing systemic infections.

It is a further object of this invention to provide a method of preventing systemic infections caused by Groups A, B, and C *Neisseria meningitidis*.

It is another object of this invention to provide a method of producing a polysaccharide-protein conjugate.

Further objects and advantages of the present invention will be clear from the description that follows.

In one embodiment, the present invention relates to a polysaccharide-protein conjugate comprising a polysaccharide and a carrier protein wherein the conjugate is capable of eliciting serum IgG and IgM antibodies to poly α(2→8) NeuNAc, or to both poly α(2→8) NeuNAc and poly α(2→9) NeuNAc, or to poly α(2→8),α(2→9) NeuNAc in a mammal or bird.

In another embodiment, the present invention relates to a pharmaceutical composition and a vaccine comprising a polysaccharide-protein conjugate in an amount sufficient to prevent systemic infections, and a pharmaceutically acceptable diluent, carrier, or excipient.

In a further embodiment, the present invention relates to a method of preventing systemic infections in an animal comprising administering to the animal an amount of a polysaccharide-protein conjugate sufficient to effect the prevention.

In another embodiment, the present invention relates to a method of preventing systemic infections caused by Groups A,-B, and C *Neisseria meningitidis* in an animal comprising administering to the animal the above-described polysaccharide-protein conjugate and a Group A meninococcal polysaccharide-protein conjugate under conditions such that the infections are prevented.

In yet another embodiment, the present invention relates to a method of producing a polysaccharide-protein conjugate comprising derivatizing a polysaccharide and conjugating the derivatized polysaccharide to a protein.

DETAILED DESCRIPTION OF THE INVENTION

The present invention relates to a polysaccharide-protein conjugate and a vaccine. This conjugate includes a polysaccharide and a carrier protein and is capable of eliciting serum IgG and IgM antibodies to poly α(2→8) NeuNAc, or to both poly α(2→8) NeuNAc and poly α(2→9) NeuNAc, or to poly α(2→8),α(2→9) NeuNAc in a mammal or bird. The carrier is associated with the polysaccharide in such a way as to increase the immunogenicity of the polysaccharide and to confer upon it the properties of both eliciting a booster response and IgG antibodies. These immunologic properties should be elicited by the protein-polysaccharide vaccine alone. Addition of adjuvants, such as aluminum salts, bacterial murein structures in saline or in emulsions, may be helpful in eliciting or in enhancing the production of poly α(2→8) NeuNAc and poly α(2→9) NeuNAc Antibodies by the *E. coli* K92 and the poly α(2→8) NeuNAc conjugate vaccines. In one preferred embodiment, the carrier protein is covalently bound to the polysaccharide. The covalent bond should preserve the immunologic properties of the native polysaccharide and native protein. Some proteins that could serve as effective carriers for covalently bound polysaccharide-protein conjugates are albumins, pharmacologically active proteins that have been detoxified, by chemical or genetic mechanisms, including diptheria, tetanus, pertussis, *Pseudomonas aeruginosa* exotoxin A and *Stapylococcus aureus* toxins, synthetic polypeptides, bacterial outer membrane proteins and viral proteins (Schneerson, R. et al. (1980) In: New Developments with Human and Veterinary Vaccines. Eds. Mizrahi et al., New York, Alan R. Liss; Schneerson, R. et al. (1987) In: Towards Better Carbohydrate Vaccines. Eds., Bell, R. & Torrigiani, G., World Health Organization, John Wiley & Sons, Ltd.). Carriers for the K92 or the poly $\alpha(2\rightarrow8)$ NeuNAc polysaccharides should be proteins that are immunogenic and elicit booster responses by themselves. Carriers should have the necessary groups that allow the synthesis of conjugates with the *E. coli* K92 or poly $\alpha(2\rightarrow8)$ NeuNAc polysaccharides. Carriers should confer the properties of increased immunogenicity and booster responses to the *E. coli* K92 and poly $\alpha(2\rightarrow8)$ NeuNAc including the formation of both IgM and IgG antibodies to these polysaccharides (Schneerson et al (1987) In: Towards Better Carbohydrate Vaccines. Eds., Bell, R. & Torrigiani, G., World Health Organization, John Wiley & Sons, Ltd.). In another preferred embodiment, the polysaccharide and protein are covalently bound by a linker. An effective linker has been found to be adipic acid dihydrazide. Other linkers could be diaminohexane, amino epsilon caproic acid, N-hydroxysuccinimide acid anhydride based heterobifunctional linkers as illustrated by N-succinimidyl 3-(2-pyridyldithio)priopionate (SPDP). Other cross-linking compounds can be used to synthesize the conjugate, provided they are not toxic and result in a conjugate that elicits poly $\alpha(2\rightarrow8)$ NeuNAc and poly $\alpha(2\rightarrow9)$ NeuNAc antibodies (Robbins, J. B. & Schneerson, R. (1990) J. Infect. Dis. 161:821–832). A linker is a molecule which may be used to covalently bind the polysaccharide to the protein. A chemical reaction with each end of the linker changes the structure of the linker. For example, after adipic acid dihydrazide chemically combines with the polysaccharide and the protein to form a conjugate, the polysaccharide and protein are bound by an adipic acid dihydrazido linkage. In another preferred embodiment, the polysaccharide comprises poly $\alpha(2\rightarrow8)$ NeuNAc or derivatives thereof. In a further preferred embodiment, the polysaccharide comprises a heteropolymer of $\alpha(2\rightarrow8),\alpha(2\rightarrow9)$ NeuNAc or derivatives thereof. In yet another preferred embodiment, the carrier protein is tetanus toxoid. Additional carrier proteins that may be used include albumins (Schneerson, R., et al. (1980) J. Exp. Med. 152, 361–376), diphtheria toxoid (Schneerson, R., et al. (1980) J. Exp. Med. 152, 361–376), and *Pseudomonas aeruginosa* exotoxin A and mutants of this protein (Fattom, A., et al. (1990) Infect. Immun. 58, 2367–2374).

In another embodiment, the present invention relates to a pharmaceutical composition comprising the above described polysaccharide-protein conjugate in an amount sufficient to prevent systemic infections including meningitis, caused by group B or group C *Neisseria meningitidis, Escherichia coli* K1, *Moraxella nonliquefaciens, Pasteurella haemolytica,* or other microorganisms containing poly $\alpha(2\rightarrow8)$ NeuNAc, poly $\alpha(2\rightarrow9)$ NeuNAc, or poly $\alpha(2\rightarrow8),\alpha(2\rightarrow9)$ NeuNAc surface antigens and a pharmaceutically acceptable diluent, carrier, or excipient. The pharmaceutical composition of the invention includes polysaccharide conjugate in a quantity selected depending on the route of administration. Although subcutaneous or intramuscular routes of administration are preferred, the above described polysaccharide-protein conjugate could also be administered by an intraperitoneal or intravenous route. One skilled in the art will appreciate that the amounts to be administered for any particular treatment protocol can be readily determined. Suitable amounts might be expected to fall within the range of 5.0 micrograms per dose to 100.0 micrograms per dose of either the polysaccharide or the protein (The ratios of polysaccharide and protein that comprise the conjugate may differ. The dosages mentioned for each component are within the expected range.).

In another embodiment, the present invention relates to a method of using the above described polysaccharide-protein conjugate to prevent the above described systemic infections. One skilled in the art will appreciate that the amounts to be administered for any particular treatment protocol can readily be determined.

In yet another embodiment, the present invention relates to a method of preventing systemic infections caused by Groups A, B, and C *Neisseria meningitidis* in an animal comprising administering to the animal the above-described polysaccharide-protein conjugate and a Group A meningococcal polysaccharide-protein conjugate under conditions such that the infections are prevented. The compositions also serve as vaccines.

In another embodiment, the present invention relates to a method of producing a polysaccharide-protein conjugate effective in eliciting serum IgG and IgM antibodies to poly $\alpha(2\rightarrow8)$ NeuNAc, or to both poly $\alpha(2\rightarrow8)$ NeuNAc and poly $\alpha(2\rightarrow9)$ NeuNAc, or to poly $\alpha(2\rightarrow8),\alpha(2\rightarrow9)$ NeuNAc in a mammal or bird. The first step of the method comprises derivatizing the polysaccharide by using, for example, adipic acid dihydrazide in a carbodiimide reaction, or alternative agents/protocols. Adipic acid dihydrazide may be substituted in the carbodiimide reaction with other dihydrazide compounds or diamino compounds (for example: diamino hexane). Other derivatives of the polysaccharides could be made in order to covalently bind them to proteins. These include the use of disulfide bonds linked by heterobifunctional reagents (Szu, S. C., et al. (1986) Infect. Immun. 54, 448–455; Szu, S. C., et al. (1987) J. Exp. Med. 166, 1510–1524).

After derivatizing the polysaccharide, the next step of the method involves conjugating the derivative to a protein. Preferably, the adipic acid hydrazide derivative of the polysaccharide is conjugated to the protein by mixing the derivative with the carrier protein at equal concentrations and adjusting the pH to a pH in the range between 6.1 and 7.0. The reactants are dissolved in 0.2M NaCl and the temperature is at 3–8° C. Then, 1-ethyl-3(3-dimethylaminopropyl)carbodiimide (EDAC) is added to a final concentration less than 0.3M. The original pH is maintained for 3 hours. Next, the reaction mixture is dialyzed against 0.2M NaCl at 3–8° C. for 3 days with multiple changes of the outer fluid. This synthetic scheme of multipoint attachment does not grossly fragment the poly $\alpha(2\rightarrow8)$ NeuNAc or poly $\alpha(2\rightarrow8),\alpha(2\rightarrow9)$ NeuNAc and may provide conformational stability to the polysaccharide.

The invention is described in further detail in the following non-limiting examples.

EXAMPLES

The following protocols and experimental details are referenced in the examples that follow:

Bacteria. *E. coli* 07:K1:H- strain C94, *E. coli* 016:K1:H-, stable in the O acetyl negative form (OAc⁻), *E. coli* 075:K1:H-, OAc⁺, strain LH, (Lars A. Hanson, Goteborg, Sweden), *E. coli* 013:K92:H4, strain N67 have been described (Robbins, J. B. et al. (1972) Infect. Immun. 6, 651–656). Group B meningococci, serotype 6, strain M990 and strain B11, and Group C meningococcus, strain C11, were provided by Carl E. Frasch, FDA, Bethesda, Md.

Polysaccharides and proteins. CP were purified from Group B meningococcus, strains B11 and M990, *E. coli* strains C94, LH, 016:K1:H- and N67 (World Health Organization Expert Committee on Biological Standardization. (1977) Technical Report Series, 610. WHO, Geneva, Switzerland). These CP contained <1.0% of protein and nucleic acid, 75 to 87% NeuNAc (Yao, K. & Ubuka, T. (1987) Acta Med. Okayama. 41, 237–241), <0.01% of LPS and had Kd values through 4B-CL Sepharose of ≈0.5 (World Health Organization Expert Committee on Biological Standardization. (1977) Technical Report Series, 610. WHO, Geneva, Switzerland). The OAc contents were 1.62 μM/mg for LH and 1.39 μM/mg for the group C meningococcal CP (Bhattacharjee, A. K. et al. (1975) J. Biol. Chem. 250, 1926–1932; World Health Organization Expert Committee on Biological Standardization. (1977) Technical Report Series, 610. WHO, Geneva, Switzerland). The $^{13}$C and proton NMR spectra of the poly α(2→8) NeuNAc and K92 CP were identical to those reported for these two polymers (Bhattacharjee, A. K. et al. (1975) J. Biol. Chem. 250, 1926–1932; Egan, W. et al. (1977) Biochem. (USA) 16, 3687–3692). Group C meningococcal CP was obtained from Pat Mcverry, Connaught Laboratories Inc, Swiftwater, Pa., and tetanus toxoid (TT), lot GYA, and group A meningococcal CP from Dominique Schulz, Pasteur Merieux Serums and Vaccines, Lyon, France. Type III, group B streptococcus CP was purified in the laboratory (Lagergard, T. et al. (1990) Infect. & Immun. 58, 687–694).

*Hyperimmune sera*. Antisera, prepared by intravenous injections of killed cells of Group B meningococci, strain B11 (horse 46), Group C meningococci, strain C11 (burro 211) and rabbit *E. coli* K92 (Drs. Ida and Frits Ørskov, Statens Seruminstitut, Copenhagen, Denmark) have been described (Ørskov, I., & Ørskov, F. (1985) J. Hyg. Camb. 95, 551–575; Allen, P. Z. et al. (1982) J. Clin. Microbiol. 15, 324–329; Glode, M. P. et al. (1977) J. Infect. Dis. 135, 94–102; Ørskov F. et al. (1979) J. Exp. Med. 149, 669–685). Mice were injected with formalin-killed cells and their sera harvested as described (Ørskov, I., & Ørskov, F. (1985) J. Hyg. Camb. 95, 551–575; Lagergard, T. et al. (1990) Infect. & Immun. 58, 687–694). Antisera for standards were produced in NIH general purpose mice by i.p. injection of 5.0 μg of either TT or K1-TT$_1$ in Freund's adjuvants (Lagergard, T. et al. (1990) Infect. & Immun. 58, 687–694).

Serology. Double immunodiffusion was performed in 0.6% agarose. ELISA was performed using biotinylated CP (Sutton, A. et al. (1985) J. Immunol. Meth. 82, 215–224). Murine sera were assayed for poly α(2→8) NeuNAc and poly α(2→9) NeuNAc and TT antibodies using alkaline-phosphatase-labeled goat anti-murine immunoglobulins (Kirkgaard & Perry Inc, Gaithersburg, Md.) (Lagergard, T. et al. (1989) Infect. & Immun. 58, 687–694; Sutton, A. et al. (1985) J. Immunol. Meth. 82, 215–224). Murine IgM mAb to poly α(2→8) NeuNAc (Wendell Zollinger, Walter Reed Army Institute of Research, Washington, D.C.) and murine IgM and IgG mAb to poly α(2→9) NeuNAc (Kathryn Stein, FDA, Rockville, Md.) were used as reference standards (Mandrell, R. E. & Zollinger, W. D. (1982) J. Immunol. 129, 2172–2178; Rubinstein, L. J. & Stein, K. E. (1988) J. Immunol. 141, 4357–4362). Human poly α(2→8) NeuNAc antibodies were assayed as described (Claesson, B. O. et al. (1988) J. Pediatr. 112, 695–702). A human IgM mAb (Elvin Kabat, Columbia University, NY) (Kabat, E. A. et al. (1986) J. Exp. Med. 164, 642–654; Kabat, E. A. et al. (1988) J. Exp. Med. 168, 699–711) and a high-titered human serum (GH) were used as references for human poly α(2→8) NeuNAc antibodies and the data are expressed as μg/ml for the IgM and as percent of the standard for IgG.

The effect of temperature upon IgG binding to poly α(2→8) NeuNAc and poly α(2→9) NeuNAc was assayed with sera from mice injected with bacteria or three times with 10.0 μg of conjugates. The data are expressed as the percent binding at 37° C. compared to 22° C.

Synthesis of conjugates. It was confirmed that treatment at pH <6.0 or with 1-ethyl-3-(3-dimethylaminopropyl) carbodiimide (EDAC) at concentrations >0.3M, even at neutral pH, resulted in loss of antigenicity of poly α(2→8) NeuNAc (Lifely, M. R., Gilbert, A. S. & Moreno, C. (1981) Carb. Res. 94, 193–201). Accordingly, the CP (5.0 mg/ml in 0.2M NaCl) were derivatized with 0.5M adipic acid dihydrazide (ADH), 0.1M EDAC, pH 6.1 to 7.0 at room temperature for 3 to 4 h. The pH was maintained in a pH stat with 0.25N HCl. The reaction mixture was dialyzed against 0.2M NaCl at 3–8° C., for 2 days with 3 changes of the outer fluid and passed through 4B-CL Sepharose in this solvent. The CP-containing fractions were pooled, dialyzed against sterile pyrogen-free water and freeze-dried. The content of adipic acid hydrazide (AH) was assayed by the TNBS reaction (Inman, J. K., & H. M. Dintzis. (1969) Biochem. (USA) 8, 4074–4080; Schneerson, R. et al. (1980) J. Exp. Med. 152, 361–376). AH-CP and TT, at equal concentrations of 7.5 to 20 mg/ml in 0.2M NaCl, were adjusted to a pH between 6.1 and 7.0 with 0.1N HCl. Then, 0.1M EDAC was added and this pH maintained at 3–8° C. for 3 h. The reaction mixture was dialyzed against 0.2M NaCl at 3–8° C. and then passed through 4B-CL Sepharose in the same solvent. The void volume fractions were pooled, assayed for NeuNAc and protein and stored in 0.01% thimerosal at 3–8° C.

Immunization of mice. General purpose mice, 4 to 5 weeks old, were injected s.c. with 2.5 μg of NeuNAc in 0.1 ml of saline, either as the CP alone or as the conjugate, 3 times 2 weeks apart (Schneerson, R. et al. (1980) J. Exp. Med. 152, 361–376). Ten mice from each group were exsanguinated 7 days after each injection. None of the mice injected with saline (controls) had antibodies to the CP or to TT (data not shown).

Adsorption. ELISA was used to determine the specificity of IgG poly α(2→8) NeuNAc and poly α(2→9) NeuNAc antibodies. Dilutions of sera that yielded an A in the upper linear part of the curve (1.0 to 1.4) were mixed with 100 μg of either poly α(2→8) NeuNAc, poly α(2→9) NeuNAc, or K92 CP and incubated at 22° C. for 2 h and overnight at 3–8° C. Controls were the group A meningococcal and the type III group B streptococcal CP (containing an α(2→8)-linked NeuNAc residue per repeat unit). Adsorption by the CP was calculated as the percent A compared to the unadsorbed sera.

Human sera. Paired maternal and cord sera were donated by James C. Parke Jr, Charlotte Memorial Hospital and Medical Center, Charlotte, N.C. and Eyal Schiff and Justin Passwell, Sheba Medical Center, Israel.

Statistical methods. Data analysis was performed using the Statistical Analysis System (SAS). The logarithms of the concentrations were used for all statistical calculations. Antibody concentrations that were below the limit of sensitivity of the ELISA were assigned values equal to one half of that value. Comparison of geometric means was performed with the two-sided t-test and the paired t-test.

Example 1

Characterization of the Conjugates

Data of representative conjugates are shown in Table 1. The percent of derivatization of the CP with AH ranged from 0.8 for K1-TT$_1$ to 10.2 for K92-TT$_2$. All AH derivatives, except for the latter, yielded an identity reaction with the native CP by double immunodiffusion. The native CP formed a spur over this K92-AH derivative (not shown).

The protein/NeuNAc ratios were related to the percent derivatization of the CP with AH. K1-TT$_1$ had the highest protein/NeuNAc ratio (12.8) and contained a CP with 0.8% AH. K92-TT$_2$, with the lowest ratio (1.4), contained a CP with 10.2% AH. The highest yields of conjugates were obtained when the reaction mixture for conjugation used concentrations of 7.5 to 10 mg/ml of TT and AH-CP.

Figure 2:
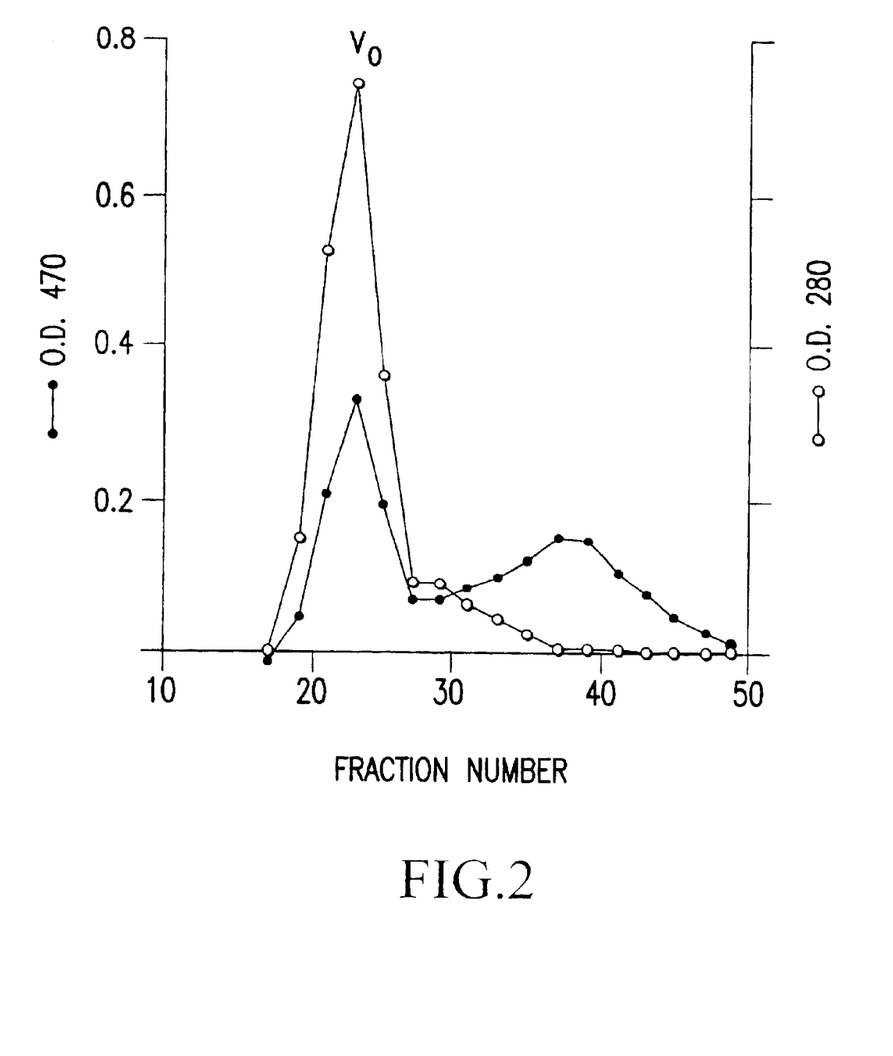
FIG. 2. Gel filtration of K92-TT$_1$(tetanus toxoid) conjugate. 1.0 ml of K92-TT$_1$, was passed through a column of 4B-CL Sepharose (2.5×90 cm) in 0.2M NaCl. The fraction size was 2.0 ml and the eluent was monitored by assay of NeuNAc (Yao, K. & Ubuka, T. (1987) Acta Med. Okayama. 41, 237–241) and by absorbance at 280 nm (World Health Organization Expert Committee on Biological Standardization. (1977) Technical Report Series, 610. WHO, Geneva, Switzerland; Schneerson, R. et al. (1980) J. Exp. Med. 152, 361–376).
Figure 3:
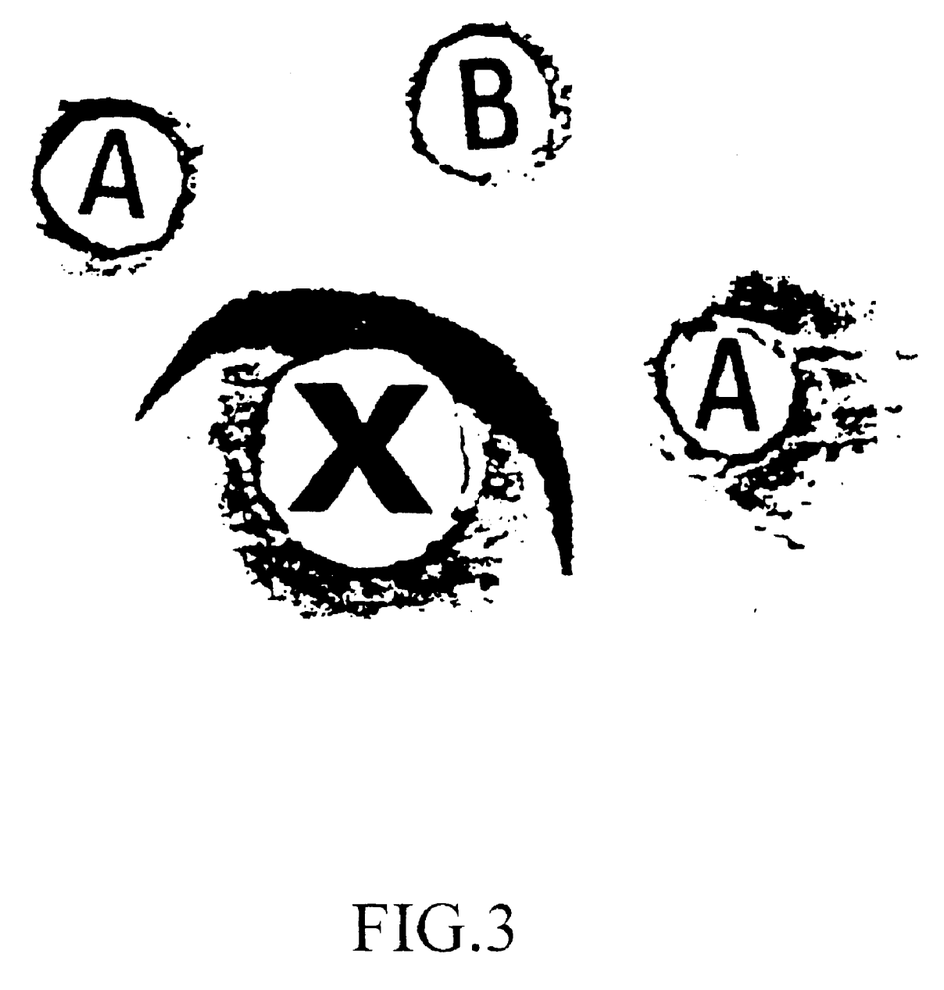
FIG. 3. Double immunodiffusion with K92 conjugate: Center well—K92-TT$_1$, 0.1 mg/ml, Well A—rabbit antiserum to *Escherichia coli* K92 cells, Well B—mouse tetanus toxin antiserum.

All preparations of conjugates eluted at the void volume through CL-4B Sepharose indicating multipoint attachment between the AH-CP and the TT (FIG. 2). FIG. 3 provides serologic evidence for the covalent attachment of the CP with the carrier protein (TT). Antiserum to each component precipitated with a line of identity with a representative conjugate, K1-TT$_1$. Non-identical lines of precipitation were formed when these antisera reacted with mixtures of the CP and TT (not shown).

TABLE 1

Characterization of capsular polysaccharide-protein conjugates

| Conjugate | Protein (μg/ml) | NeuNAc (μg/ml) | AH/Neu-NAc (wt/wt) | Protein/CP ratio | Yield (% CP) | Concentration (mg/ml)* |
|---|---|---|---|---|---|---|
| K1-TT$_1$** | 531 | 41.4 | 0.8 | 12.8 | 5.0 | 20 |
| K1-TT$_2$** | 465 | 96.1 | 2.6 | 4.8 | 9.6 | 15 |
| K1$_{OAc+}$-TT*** | 630 | 262 | 1.9 | 2.4 | 28.8 | 10 |
| MenB-TT$_1$ | 463 | 94.5 | 1.8 | 4.9 | 5.0 | 15 |
| MenB-TT$_2$ | 314 | 51.1 | 2.3 | 6.2 | 4.6 | 15 |
| K92-TT$_1$ | 294 | 98.8 | 3.4 | 3.0 | 10.5 | 15 |
| K92-TT$_2$ | 705 | 517 | 10.2 | 1.4 | 51.7 | 7.5 |
| MenC-TT | 234 | 121 | 8.5 | 1.9 | 22.5 | 10 |

*Concentration of the reactants during the conjugation procedure.
**The K1 CP for these conjugates were OAc$^-$.
***K1 CP of the OAc$^+$ variant of *Escherichia coli*, strain LH.

Example 2

Induction of Poly α(2→8) NeuNAc Antibodies (Table 2)

The four CP did not elicit rises of IgM or IgG antibodies. All four poly α(2→8) NeuNAc conjugates (K1-TT$_1$, K1-TT$_2$, MenB-TT$_1$ and MenB-TT$_2$) elicited statistically significant rises in IgM antibodies. An IgM booster response was elicited after the second injection by these conjugates; the levels elicited by K1-TT$_1$ and MenB-TT$_1$ were higher than those elicited by the other two poly α(2→8) NeuNAc conjugates (p<0.001). Only K1-TT$_2$ and MenB-TT$_2$ elicited IgM booster responses after the third injection.

The four poly α(2→8) NeuNAc conjugates elicited statistically significant rises of IgG antibodies after the second and third injections. The IgG levels elicited by the third injection of MenB-TT$_2$ (4.29 U/ml) were higher than those elicited by the other three conjugates but not significant (NS). One mouse in this group, however, had 240 U/ml and the geometric mean level, excluding this animal, was 2.74 U/ml.

K1$_{OAc+}$-TT, prepared from *E. coli* strain LH, elicited high levels of IgM and IgG antibody to the OAc$^+$ variant of this CP and low antibody levels to poly α(2→8) NeuNAc.

The two K92-TT elicited both IgM and IgG poly α(2→8) NeuNAc antibodies; the IgG levels were higher than those elicited by the K1-TT$_1$ (P=0.01), K1-TT$_2$ (P=0.0001), MenB-TT$_1$ (P=0.0002) and MenB-TT2 (p<0.05). K92-TT2, containing the heavily derivatized K92 CP, also elicited higher IgG antibody levels than the K1-TT and MenB-TT conjugates.

MenC-TT did not elicit poly α(2→8) NeuNAc antibodies in any of the mice.

The specificity of the antibodies was shown by adsorption experiments using sera from mice injected with killed bacteria or by three injections of the conjugates (data not shown). Poly α(2→8) NeuNAc and poly α(2→9) NeuNAc adsorbed homologous IgG antibodies from the antisera (50–89%). The K92 CP adsorbed both poly α(2→8) and poly α(2→9) NeuNAc antibodies (69–89%). The two controls (group A meningococcal and group B type III streptococcal CP) adsorbed <10% of either poly α(2→8) or α(2→9) NeuNAc antibodies.

TABLE 2

Serum IgG and IgM antibodies to the capsular polysaccharide of Group B *Neisseria meningitidis* and *Escherichia coli* K1 (poly α(2→8) NeuNAc).

Post-immunization geometric mean

| Immunogen | IgM (μg/ml) | | | IgG (ELISA U) | | |
|---|---|---|---|---|---|---|
| | 1st | 2nd | 3rd | 1st | 2nd | 3rd |
| K1 | 0.09 | 0.12 | 0.11$^a$ | 0.05 | 0.05 | 0.06$^c$ |
| K1-TT$_1$ | 0.32 | 3.35 | 1.63$^b$ | 0.10 | 0.49 | 2.44$^d$ |
| K1-TT$_2$ | 0.12 | 0.19 | 0.62$^b$ | 0.06 | 0.13 | 1.95$^e$ |
| K1$_{OAc+}$-TT* | 0.17 | 0.16 | 0.08 | 0.07 | 0.20 | 0.72 |
| | 38.7 | 27.2 | 7.18 | 0.16 | 12.1 | 56.1 |
| MenB | 0.05 | 0.05 | 0.05$^a$ | 0.05 | 0.05 | 0.05$^c$ |
| MenB-TT$_1$ | 0.67 | 1.59 | 1.50$^b$ | 0.08 | 0.45 | 1.81$^f$ |
| MenB-TT$_2$ | 0.08 | 0.26 | 0.72$^b$ | 0.05 | 0.11 | 4.29$^g$ |
| K92 | 0.05 | 0.05 | 0.05$^a$ | 0.05 | 0.05 | 0.05$^c$ |
| K92-TT$_1$ | 0.09 | 0.49 | 1.20$^b$ | 0.05 | 0.25 | 17.2$^h$ |
| K92-TT$_2$ | 0.28 | 0.78 | 0.47$^b$ | 0.05 | 0.83 | 4.52$^i$ |
| MenC | 0.05 | 0.05 | 0.05 | 0.05 | 0.05 | 0.05 |
| MenC-TT | 0.05 | 0.05 | 0.05 | 0.05 | 0.05 | 0.05 | b vs a: P < 0.001, h vs i: P = 0.007, h vs g: P < 0.05, h vs f, e: P < 005, h vs d: P = 0.01
*The second set of values for conjugate K1$_{OAc+}$-TT was determined using OAc$^+$ K1 CP as the antigen.

Example 3

Induction of Poly α(2→9) NeuNAc and TT Antibodies (Table 3)

The homologous CP induced low levels of poly α(2→9) NeuNAc IgM antibodies. Neither the homologous nor the heterologous CP induced IgG antibodies.

All the conjugates elicited IgM antibodies after the first injection. These levels declined after the 2nd and 3rd injections of the MenC-TT and K92-TT conjugates and increased only after the first two injections of the K1-TT conjugates.

Only the MenC-TT elicited poly α(2→9) NeuNAc IgG antibodies after the first injection; all the conjugates elicited increases after the second and third injections. The highest levels were elicited by MenC-TT>K92-TT>K1-TT. Similar to those observed with poly α(2→8) NeuNAc antibodies, the IgG antibody levels elicited by K92-TT$_1$ were higher than those elicited by K92-TT$_2$ but N.S.

TT antibodies were elicited by all the conjugates with booster responses after each injection similar to those reported for other conjugates using this protein as a carrier (data not shown) (Robbins, J. B., & Schneerson, R. (1990) J. Infect. Dis. 161, 821–832; Lagergard, T. et al. (1990) Infect. & Immun. 58, 687–694).

TABLE 3

Serum IgG and IgM antibodies (μg/ml) to the capsular-polysaccharide of group C *Neisseria meningitidis* (poly α (2→9) NeuNAc)

| | Post-immunization geometric mean | | | | | |
|---|---|---|---|---|---|---|
| | IgM | | | IgG | | |
| Antigen | 1st | 2nd | 3rd | 1st | 2nd | 3rd |
| K1 | 0.05 | 0.05 | 0.05$^a$ | 0.05 | 0.05 | 0.05$^e$ |
| K1-TT$_1$ | 0.11 | 0.32 | 0.14$^b$ | 0.05 | 0.14 | 1.24$^f$ |
| K1-TT$_2$ | 0.23 | 1.09 | 0.40$^b$ | 0.05 | 0.97 | 3.32$^f$ |
| MenC | 0.05 | 0.08 | 0.11$^c$ | 0.07 | 0.10 | 0.05$^e$ |
| MenC-TT | 2.26 | 0.89 | 0.53$^d$ | 1.87 | 18.4 | 107.5$^g$ |
| K92 | 0.05 | 0.05 | 0.05$^a$ | 0.05 | 0.05 | 0.05$^e$ |
| K92-TT$_1$ | 3.23 | 2.85 | 0.68$^b$ | 0.05 | 0.70 | 21.4$^h$ |
| K92-TT$_2$ | 1.87 | 0.74 | 0.15$^b$ | 0.06 | 1.71 | 15.9$^h$ | b vs a: P = 0.0001, d, vs c: P = 0.0004, c vs a: P < 0.001, f,g,h vs e: P = 0.0001, g vs f,h: P < 0.001

Example 4

Temperature-dependent Binding of IgG Antibodies (Table 4)

Binding to the two CP by IgG antibodies elicited by K92-TT, K1-TT and MenC-TT conjugates and *E. coli* K92 and *M. nonliguefaciens* cells was assayed at 22° C. and at 37° C. Reduction in binding at 37° C. of poly α(2→8) NeuNAc antibodies elicited by the K1-TT$_2$, *M. nonliquefaciens,* and K92-TT$_1$ was similar (≈40%). In contrast, there was only ≦10% reduction in binding of poly α(2→9) NeuNAc antibodies elicited by K1-TT$_2$, K92-TT$_1$, MenC-TT and *E. coli* K92 cells. These data are consistent with other results (Mandrell, R. E. & Zollinger, W. D. (1982) J. Immunol. 129, 2172–2178).

TABLE 4

Temperature-dependent binding of murine poly α(2→8) and poly α(2→9) NeuNAc IgG antibodies (percent binding at 37° C. compared to 22° C.)

| | CP Used for ELISA | |
|---|---|---|
| Immunogen | poly α(2→8) NeuNAc | poly α(2→9) NeuNAc |
| K1-TT$_2$ | 41.8% | 90.9% |
| *M. nonliquefaciens* cells | 34.6% | N.D.* |
| K92-TT$_1$ | 49.1% | 93.8% |
| *E. coli* K92 cells | N.D. | 91.5% |
| MenC-TT | N.D. | 100% |

*N.D. Not detectable

Example 5

Poly α(2→8) NeuNAc Antibodies in Paired Maternal and Cord Sera (Table 5)

Most women at term had detectable IgM and IgG poly α(2→8) NeuNAc antibodies. The IgM and IgG levels of the Israeli women were higher than those of the women in Charlotte, N.C. (P=0.0001). As expected, the IgM poly α(2→8) NeuNAc antibodies in the cord were at trace or non-detectable levels. The geometric mean (GM) levels of IgG antibodies in the cord sera were significantly higher than those of the mothers from both regions. Most of the cord poly α(2→8) NeuNAc IgG antibodies were higher than those of the corresponding maternal sera (69/81).

TABLE 5

IgG and IgM antibodies to poly α(28) NeuNAc in paired human mother-newborn (umbilical cord) sera (Geometric mean)

| | | Maternal | | Cord | | Maternal IgG |
|---|---|---|---|---|---|---|
| Source | n | IgM | IgG | IgM | IgG | vs cord IgG |
| Charlotte, NC | 36 | 0.35 | 26.9 | 0.03 | 32.9 | P = 0.003 |
| Sheba Medical Center, Israel | 45 | 0.91 | 80.0 | 0.04 | 121 | P = 0.0001 |

The levels of IgM antibodies are expressed as μg Ab/ml and the levels of IgG antibodies as percent of a high-titered adult serum (GH) as ELISA units.

Example 6

Passive Immunization

Either monoclonal or polyclonal antibodies, of human or animal origin, for passive immunization for prevention, or as adjunct therapy of systemic infections with organisms containing poly α(2→8) NeuNAc or poly α(2→9) NeuNAc surface antigens in an animal, including humans, may be produced by the above-described conjugate vaccines. (example: passive immunization of case contacts of group B meningococcal systemic infections including meningitis). Passive immunization, for both therapeutic and preventative purposes, has been carried out since the turn of the century. Passive immunization has been considered again for prevention of group B meningococcus systemic infections including meningitis, as well as other capsulated bacterial pathogens that cause systemic infections including the pneumococcus, Haemophilus influenzae type b, group B streptococcus and *E. coli* infections in hosts at higher risk than the general population including fetuses, newborns and patients with congenital or acquired immunodeficiencies (Patients with immunodeficiencies may not be capable of producing protective levels of antibodies when injected with K92 and/or poly α(2→8) NeuNAc conjugate vaccines). The technique of passive immunization is taught by: Flexner (1913) J. Exp. Med. 17:553–570; Brahahm (1938) Proc. Soc. Exp. Biol. Med. 30:348; Raff et al. (1988) J. Infect. Dis. 157:118–126; Kim et al. (1985) Infect. Immun. 50:734–737; and Latson et al. (1988) Podiatr. Infect. Dis. 7:747–752.

Example 7

Further Uses of the Antibodies

Either monoclonal or polyclonal antibodies are prepared for diagnostic purposes or for the investigation of the developmental processes, pathogenesis, prevention, immunopathology, or immunologic responses of poly α(2→8) NeuNAc, poly (2→9) NeuNAc, or to poly α(2→8), α(2→9) NeuNAc alone, as a component or a complex molecule or of organisms containing these saccharides. The use of poly α(2→8) NeuNAc antibodies, especially of the IgG class, for use in developmental studies is illustrated in the following articles: Husmann et al. (1990) J. Histochem. & Cytol. 38:209–215; Robbins & Schneerson (1990) J. Infect. Dis. 161:821–832). The above-described conjugate-induced antibodies may be derivatized or interacted with other substances to produce kits for diagnosis of diseases or identification of organisms containing poly α(2→8) NeuNAc or poly α(2→9) NeuNAc. Kits, containing polyclonal or monoclonal antibodies, are used worldwide for the diagnosis of systemic infections, including meningitis, or for asymptomatic carriers of *Neisseria meningitidis* as well as other capsulated bacterial pathogens. This use is reviewed in: Lim et al. (1990) J. Clin. Microbiol. 28:670–675; Cuevas et al. (1989) Ann. Trop. Med. Parasitol. 83:375–379; Ørskov et al. (1979) J. Exp. Med. 149:669–685.

Example 8

Active Immunization Against the Three Major Serogroups of *N. meningitidis*

Active immunization against the three major serogroups of *Neisseria meningitidis*, would include conjugate vaccines of group A along with the conjugate vaccines described-above. A trivalent polysaccharide-protein conjugate vaccine, capable of eliciting serum antibodies to groups A, B, and C meningococcal meningitis and thereby preventing most of the systemic infections, including meningitis, caused by *Neisseria meningitidis,* may be produced by this method using the above-described conjugates and a group A meningococcal conjugate. Group A meningococcal polysaccharide protein conjugates have been synthesized according to a published method (Chu et al. (1983) Infect. Immun. 40:245–256). Concurrent injection of more than one polysaccharide protein conjugate in animals and in humans has been shown to elicit protective levels of antibodies to each component at levels equal to those elicited by each conjugate injected separately (Schneerson et al. (1986) Infect. Immun. 52:501–518).

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. An *Escherichia coli* K92 capsular polysaccharide and carrier protein conjugate, wherein said polysaccharide and said carrier protein are covalently coupled with a linker selected from the group consisting of adipic acid dihydrazide, diaminohexane, amino epsilon caproic acid, and N-hydroxysuccinimide acid anhydride-based heterobifunctional molecules, and further wherein said conjugate elicits the production of antibodies reactive with poly α(2→8)NeuNAc capsular polysaccharides of *Escherichia coli* K1 and group B *N. meningitidis* and with poly α(2→9) NeuNAc polysaccharide of Group C *N. meningitidis* microorganisms, and antibodies reactive with said carrier protein.

2. The conjugate according to claim 1, wherein said carrier protein is immunogenic and is selected from the group consisting of albumin, chemically or genetically detoxified diphtheria toxin, tetanus toxoid, detoxified exotoxin A of *Pseudomonas aeruginosa,* detoxified *Staphylococcus aureus* toxin, synthetic polypeptides, bacterial outer membrane proteins, and viral proteins.

3. The conjugate according to claim 2, wherein said carrier protein is tetanus toxoid.

4. The conjugate according to claim 1, wherein said linker is adipic acid dihydrazide.

5. An *Escherichia coli* K92 capsular polysaccharide and tetanus toxoid conjugate, wherein said polysaccharide is covalently coupled to detoxified tetanus toxin with a linker selected from the group consisting of adipic acid dihydrazide, diaminohexane, amino epsilon caproic acid, and N-hydroxysuccinimide acid anhydride-based heterobifunctional molecules, and further wherein said conjugate elicits the production of antibodies reactive with poly α(2→8)NeuNAc capsular polysaccharides of *Escherichia coli* K1 and group B *N. meningitidis* and with poly α(2→9) NeuNAc polysaccharide of Group C *N. meningitides* microorganisms, and antibodies reactive with tetanus toxoid protein.

6. The conjugate according to claim 5, wherein said linker is adipic acid digydrazide.

7. A poly α(2→8), α(2→9)NeuNAc containing polysaccharide and protein conjugate comprising a poly α(2→8), α(2→9)NeuNAc capsular polysaccharide component coupled to an immunogenic carrier protein component with a linker selected from the group consisting of adipic acid dihydrazide, diaminohexane, amino epsilon caproic acid, and N-hydroxysuccinimide acid anhydride-based heterobifunctional molecules, wherein said conjugate elicits the production of antibodies reactive with poly α(2→8) NeuNAc capsular polysaccharides of *Escherichia coli* K1 and group B *N. meningitidis* and with poly α(2→9)NeuNAc polysaccharide of Group C *N. meningitidis* microorganisms, and antibodies reactive with said carrier protein.

8. The conjugate according to claim 7, wherein said carrier protein is immunogenic and is selected from the group consisting of albumins, chemically or genetically detoxified diphteria toxin, tetanus toxoid, detoxified exotoxin A of *Pseudomonas aeruginosa,* detoxified *Staphylococcus aureus* toxin, synthetic polypeptides, bacterial outer membrane proteins, and viral proteins.

9. The conjugate according to claim 8, wherein said carrier protein is tetanus toxoid.

10. The conjugate according to claim 7, wherein said linker is adipic acid dihydrazide.

11. A method of producing serum antibodies immunoreactive with poly α(2→8)NeuNAc-containing capsular polysaccharides of *Escherichia coli* K1 and Group B meningococci, antibodies reactive with poly α(2→9) NeuNAc-containing capsular polysaccharide of Group C meningococci, and antibodies reactive with a carrier protein, comprising the steps of:

a) providing a conjugate according to claim 1, claim 5, or claim 7;

b) administering said conjugate to said mammal; and c) boosting said mammal with said conjugate to produce said immunoreactive anti-polysaccharide antibodies and said anti-carrier protein antibodies.

12. The method according to claim 11, wherein said carrier protein of the conjugate of step a) is immunogenic and is selected from the group consisting of albumins, chemically or genetically detoxified diphtheria toxin, tetanus toxoid, detoxified exotoxin A of *Pseudomonas aeruginosa,* detoxified *Staphylococcus aureus* toxin, synthetic polypeptides, bacterial outer membrane proteins, and viral proteins.

13. The method according to claim 12, wherein said carrier protein is tetanus toxoid.

14. A method of immunizing a mammal to produce antibodies reactive with the capsular polysaccharide surface antigens of microorganisms containing poly α(2→8)

NeuNac polysaccharides, antibodies reactive with the capsular polysaccharide surface antigens of microorganisms containing poly α(2→9)NeuNac polysaccharide, and antibodies reactive with a carrier protein, comprising administering to said mammal a conjugate comprising *E. coli* K92 capsular polysaccharide linked to a carrier protein, under conditions suitable for eliciting said anti-polysaccharide and anti-carrier protein antibodies wherein said conjugate is the conjugate of claim 1, claim 5.

15. The method according to claim 14, wherein said microorgansims containing poly α(2→8)NeuNAc polysaccharides are *Escherichia coli* K1 and *Neissertiae meningitidis* Group B, and wherein said microorganisms containing poly α(2→9)NeuNAc polysaccharide are *Neisseriae meningitidis* Group C.

16. An immunogenic preparation comprising the conjugate according to claim 1, claim 5, or claim 7 in a pharmaceutically-acceptable carrier, diluent, adjuvant, excipient, or mixtures thereof.

17. The preparation according to claim 16, wherein said carrier protein is immunogenic, elicits a booster response, and confers said immunogenicity and said booster response to said conjugate.

18. A vaccine comprising the polysaccharide and carrier protein conjugate according to claim 1, claim 5, or claim 7, said vaccine capable of being administered in an amount effective to elicit in a mammal antibodies reactive with poly α(2→8)NeuNAc capsular polysaccharides and with poly α(2→9)NeuNAc capsular polysaccharides of bacterial microorganisms.

19. The vaccine according to claim 18, wherein said carrier protein is immunogenic, elicits a booster response, and confers said immunogenicity and said booster response to said conjugate.

20. The vaccine according to claim 19, wherein said carrier protein is selected from the group consisting of albumins, chemically or genetically detoxified diphtheria toxin, tetanus toxoid, detoxified exotoxin A of *Pseudomonas aeruginosa*, detoxified *Staphylococcus aureus* toxin, synthetic polypeptides, bacterial outer membrane proteins, and viral proteins.

21. The vaccine according to claim 20, wherein said carrier protein is tetanus toxoid.

22. Antibodies raised against said polysaccharide-protein conjugates according to claim 1, claim 5, or claim 7.

23. The antibodies according to claim 22, wherein said antibodies are selected from the group consisting of the IgM and IgG classes.

24. A method of passively immunizing a mammal to protect against infection from microorganisms containing poly α(2→8)NeuNAc capsular polysaccharides and with microorganisms containing poly α(2→9)NeuNAc capsular polysaccharides, comprising:

a) providing a conjugate comprising *E. coli* K92 capsular polysaccharide linked to a carrier protein;

b) producing antibodies directed against said conjugate of step a); and c) administering said antibodies of step b) to a mammal wherein said conjugate is the conjugate of claim 1, claim 5.

25. A pharmaceutical composition comprising said polysaccharide-protein conjugate according to claim 1, claim 5, or claim 7 in a pharmaceutically acceptable carrier, excipient, or diluent.

26. The pharmaceutical composition according to claim 25, wherein said composition is capable of being administered in an amount effective to elicit the production of IgM and IgG antibodies reactive with poly α(2→8)NeuNAc capsular polysaccharides of *Escherichia coli* K1 and Group B *Neisseriae meningitidis*, with poly α(2→9)NeuNAc capsular polysaccharide of Group C *Neisseriae meningitidis*, and with said carrier protein.

27. A method of producing a polysaccharide-carrier protein conjugate, said conjugate effective for eliciting serum IgM and IgG antibodies immunoreactive with poly α(2→8) NeuNAc-containing polysaccharides of *Escheilchia coli* K1 and Group B *Neisseriae meningitidis*, with poly α(2→8) NeuNAc-containing capsular polysaccharide of Group C meningococci, and with said carrier protein, wherein said polysaccharide of the conjugate is the capsular polysaccharide of *E. coli* K92, comprising the steps of:

a) derivatizing said K92 polysaccharide with a linker; and b) covalently binding said derivatized polysaccharide of step a) to said carrier protein to form said immunoreactive conjugate.

28. The method according to claim 27, wherein said linker is selected from the group consisting of adipic acid dihydrazide, diaminohexane, amino epsilon caproic acid, and N-hydroxysccinimide acid anhydride-based heterobifunctional molecules.

29. The method according to claim 28, wherein said linker is adipic acid dihydrazide.

30. The method according to claim 28, wherein said carrier protein of step b) is selected from the group consisting of albumins, chemically or genetically detoxified diphtheria toxin, tetanus toxoid, pertussis toxoid, detoxified exotoxin A of *Pseudomonas aeruginosa* detoxified *Staphylococcus aureus* toxin, synthetic polypeptides, bacterial outer membrane proteins, and viral proteins.

31. The method according to claim 30, wherein said said carrier protein is tetanus toxoid.

32. The conjugate according to claim 1, wherein said diamino linker compound is diamino hexane.

33. The conjugate according to claim 1, wherein said N-hydroxysuccinimide acid anhydride-based heterobifunctional molecule is N-succinimidyl 3-(2-pyridyldithio) proprionate.

34. The conjugate according to claim 5, wherein said N-hydroxysuccinimide acid anhydride-based heterobifunctional molecule is N-succinimidyl 3-(2-pyridyldithio) proprionate.

35. The conjugate according to claim 7, wherein said N-hydroxysuccinimide acid anhydride-based heterobifunctional molecule is N-succinimidyl 3-(2-pyridyldithio) proprionate.

36. The method according to claim 28, wherein said diamino compound is diaminohexane.

37. The method according to claim 28, wherein said N-hydroxysuccinimide acid anhydride-based heterobifunctional molecule is N-succinimidyl 3-(2-pyridyldithio) proprionate.

38. A method of producing a polysaccharide-carrier protein conjugate, said conjugate effective for eliciting serum IgM and IgG antibodies immunoreactive with poly α(2→8) NeuNAc-containing polysaccharides of *Escherichia coli* K1 and Group B *Neisseriae meningitidis*, with poly α(2→8) NeuNAc-containing capsular polysaccharide of Group C meningococci, and with said carrier protein, wherein said polysaccharide of the conjugate is the capsular polysaccharide of *E. coli* K92, comprising the steps of:

a) derivatizing said K92 polysaccharide with a linker selected from the group consisting of adipic acid dihydrazide or diamino hexane, amino epsilon caproic acid, and N-hydroxysuccinimide acid anhydride-based heterobifunctional molecules; and b) covalently binding said derivatized polysaccharide of step a) to said carrier protein to form said immunoreactive antibody-eliciting conjugate.

* * * * *